United States Patent [19]

Maddox

[11] 4,306,810
[45] Dec. 22, 1981

[54] APPARATUSES AND METHOD FOR PALEOCURRENT DIRECTION DETERMINATION USING REFLECTED LIGHT

[76] Inventor: Darryl W. Maddox, 2604 6th Ave., Canyon, Tex. 79015

[21] Appl. No.: 905,353

[22] Filed: May 12, 1978

[51] Int. Cl.³ .............................................. G01N 21/23
[52] U.S. Cl. ...................................... 356/369; 356/33
[58] Field of Search ............................... 356/364–370, 356/31, 33–35; 250/225

[56] References Cited

PUBLICATIONS

Sippel, R. F., "Quartz Grain Orientations-1 (The Photometric Method)," Jr. of Sedimentary Petrology, vol. 41 #1, 3-1971, pp. 38–59.
Elshazly–Zaghloul et al., "Explicit Solution for the Optical Properties of a Uniaxial Crystal in Generalized Ellipsometry" Surface Science, vol. 56, 1976, pp. 281–292.
Azzam et al., "Application of Generalized Ellipsometry to Anisotropic Crystals", Jr. Op. Soc. America, vol. 65, 4-1975, p. 462.

Primary Examiner—John K. Corbin
Assistant Examiner—Wm. H. Punter
Attorney, Agent, or Firm—Ely Silverman

[57] ABSTRACT

A reflected light method of paleocurrent determination uses laser light source for investigation of paleocurrent direction for oriented sandstone samples from surface and from drill cores. The technique determines the average optic axis orientation by the variations in the intensity of a beam of reflected light from a polished surface of the sample as the sample is rotated.

12 Claims, 18 Drawing Figures

APPARATUSES AND METHOD FOR PALEOCURRENT DIRECTION DETERMINATION USING REFLECTED LIGHT

BACKGROUND OF THE INVENTION

The field of art to which this invention relates is measurement, testing, and core analysis.

PRIOR ART

The prior art has not provided any reliable method of measuring paleocurrent direction. While relations of grain length to optical axis of quartz crystals have been known no method or apparatus for application of such information has been provided to indicate paleocurrent direction and trend.

Such prior art is represented by U.S. Pat. Nos. 2,963,641 to R. H. Nanz, issued Dec. 6, 1960 2,963,642 to J. L. Arbogast issued Dec. 6, 1960 3,475,679 to K. S. Desseyes issued Oct. 28, 1960 3,151,292 to W. R. Orr issued Sept. 29, 1964, and by the following literature:

Martinez, Joseph D., "Photometer Method for Studying Quartz Grain Orientation" *Bulletin of the American Association of Petroleum Geologist,* V. 42, P. 588 (1958).

Martini, I. P., "A Test of Validity of Quartz Grain Orientation as a Paleocurrent and Paleoenvironmental Indicator," *Journal of Sedimentary Petrology,* V. 41, P. 60 (1971).

Sippel, R. F., "Quartz Grain Orientations-1 (The Photometric Method)" *Journal of Sedimentary Petrology,* V. 41, p. 38 (1971).

Winkelmolen, A. M., "Dielectric Anisotropy and Grain Orientation" *The American Association of Petroleum Geologists Bulletin,* V. 56/11, p. 2150 (1972).

SUMMARY OF THE INVENTION

The method determines the average optic axis orientation by measuring the variation in the intensity of a beam of light from a laser ($\lambda = 6328$ A) reflected from a polished surface of the sample. The light intersects the surface at Brewster's angle for the $\epsilon$-ray of quartz and as a result the reflected ray has a minimum intensities when the average optic axis of the sand grains lies in the plane of incidence. The two minima are not separated by 180° nor are they of equal intensity. Thereby, paleocurrent direction is determined rather than just paleocurrent trend.

Data from several groups of samples were collected. The data shows that the method accurately determined the paleocurrent direction for the samples tested.

BRIEF DESCRIPTION OF THE DRAWINGS

In FIGS. 3–12 the hatched areas represent the data of the histograms from reflected light data; these hatched areas are 3A and 3B in FIG. 3, areas 4A and 4B in FIG. 4, areas 7A and 7B in FIG. 7, areas 9A and 9B in FIG. 9, areas 10A and 10B in FIG. 10.

The areas in outline as 3C and 3D in FIG. 3, 4C and 4D in FIG. 4, 7C and 7D in FIG. 7, 9C and 9D in FIG. 9, 10C and 10D in FIG. 10 are conventional symmetrical data arrangements. These histograms are presented on the same figures for the purpose of contrast to show the greater significance (especially in view of the data of Table 1) of the reflected light data than a conventional measurement data, as well as to show the data obtained.

BACKGROUND AND THEORY OF METHODS

In addition to the reflected light method developed for the process of this invention other methods of thin section analysis maybe used to examine samples.

These other methods may also be used to verify the reflected light data.

The thin section methods use light transmitted through the thin sections. They are divided into two groups, (a) individual grain, and (b) multiple grain, depending on whether each reading gives the orientation of (a) one grain or (b) the average orientation of many grains.

In the long axis method a standard thin section is placed on the microscope stage and the stage rotated until the longest dimension of the one grain under the cross-hair is aligned in a chosen direction. The orientation is then read from the vernier on the microscope stage. The slide is then moved until a new grain is under the cross-hair and the procedure is repeated until 50–250 readings have been taken. Since there is a large scatter in the data histograms of the readings are then made. The smallest histogram interval found to be useful in this study was 20 degrees. Fifty readings provided histograms of sufficient resolution to check the reflected light data.

A light beam passing in a random direction into a non-isotropic mineral will be doubly refracted causing two beams whose E vibrations are mutually perpendicular. When viewing a hexagonal crystal down the c axis no double refraction is seen and this is the only direction for which no double refraction is seen. The c axis defines and is equivalent to the optic axis for a mineral in the hexagonal system. In this system the crystallographic axis, the c axis, and the optic axis are identical. The name chosen is determined by the context of the discussion.

The two rays generated by the double refraction are called the $\epsilon$-ray and the $\omega$-ray. They are refracted at different angles and therefore they travel at different velocities through the crystal.

The crystal has two primary refractive indices determined by the orientation of the E vibration relative to the optic axis. The $\epsilon$-ray has E vibrating in a plane parallel to the optic axis and is restricted to one direction. The $\omega$-ray has E vibrating perpendicular to the optic axis.

Most petrographic microscopes are built to accept a gypsum plate in the light path. The gypsum plate is made from crystal cut coplaner with the plane formed by the two vibration directions. The plate is oriented in the holder so that its "slow" direction is NE-SW when inserted in the microscope. When the nichols are crossed, a second-order red ($\lambda = 5500$ A) interference color is observed. With a thin section of a quartz crystal cut with its optic axis in a horizontal plane placed on the stage and the optic axis pointing NE-SW, an increased birefrengence results and the interference color is second-order blue ($\lambda = 6500$ A). Rotating the microscope stage 90 degrees so that the quartz crystal optic axis is NW-SE results in reducing the birefrengence and the observed interference color is first-order yellow ($\lambda = 4500$ A). Thus when either a yellow or blue color is observed the direction of the quartz crystal optic axis is determined.

This procedure can be extrapolated to using a thin section of a sandstone in which the optic axis are nearly parallel. A blue filter in the microscope is located so that when the optic axis of the observed quartz crystal in the section was oriented NE-SW no light was transmitted therethrough. Then place a photocell on the occular of the microscope and note the orientations of the microscope stage when minimum readings were observed on the voltmeter measuring the current from the photocell.

Figure 2:
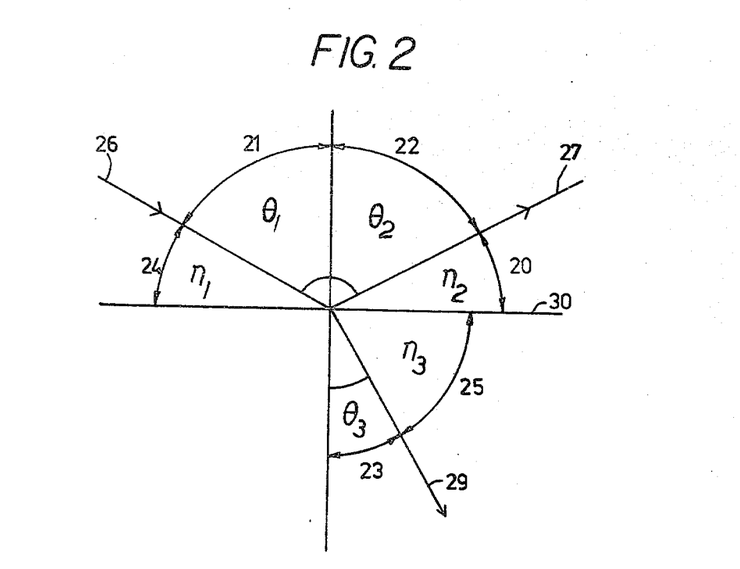
FIG. 2 is a diagramatic showing of optical relations in the apparatuses used in this invention.

A light beam 26 intersecting a partly transmitting boundary as a quartz crystal is both refracted and reflected as determined by Snell's law (FIG. 2). The intensities of the beams vary from total reflection to total refraction. Referring to FIG. 2 of the drawings, if the angle of incidence is chosen such that the reflected and refracted beams, 27 and 29, are separated by 90 degrees the intensity of the vertically polarized component of the reflected beam 27 will be zero. The angle of incidence at which the reflected beam intensity is zero is called Brewster's angle. For $\eta_3$ equals 1.5524, which corresponds to the index of refraction of the $\epsilon$ ray of quartz at a wavelength of 6328 A., Brewster's angle is about 57.29 degrees. If $\theta_1$, is not precisely Brewster's angle the reflected intensity will not be zero but will be a minimum.

FIG. 2 shows the angles of reflection and refraction as determined by Snell's Law, and wherein 21 ($\theta_1$) is the angle of incidence—Brewster's Angle;
22 ($\theta_2$) is the angle of reflection;
23 ($\theta_3$) is the angle of refraction;
24 ($\eta_1$) is the index of refraction for air;
25 ($\eta_3$) is the index of refraction for the $\epsilon$ ray of quartz.

DESCRIPTION OF THE PREFERRED EMBODIMENT

Figure 1:
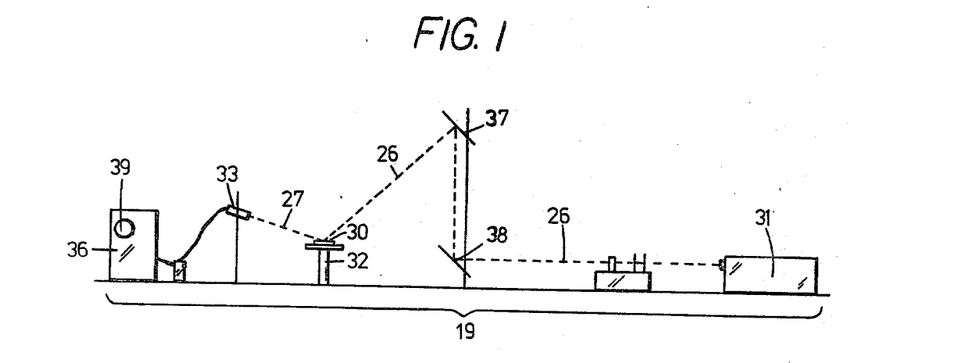
FIG. 1 is a diagramatic view of one embodiment of equipment according to this invention.

In the reflected light method, in apparatus 19 of FIG. 1 source for this method was a Spectra Physics model 132 Helium-Neon laser 31 which emits 1 mw at 6328 A. The beam 26 was focused by two lenses provided with the laser. In apparatus of FIG. 1 the correct angle of incidence was achieved by reflecting the laser beam from two stainless steel mirrors 37 and 38. Brewster's angle as constructed by establishing the appropriate ratio for the base and altitude of the right triangle formed by the equipment 32, 37, and 38.

In apparatus of FIG. 1 the correct angle of incidence was established by angle at support 32.

The sample 30 being examined was supported initially on a disk mounted on a rotable base 32. The micrometer cross-feed which held the sample on the disc was from a Leitz petrographic microscope which was used in the thin section examinations of the samples. The cross-feed held the sample and provided a reliable means for right angle movement of the sample in a horizontal plane.

The intensity of the reflected light was measured by a Metrologic Instruments photocell 33. The output from the photocell provided the input signal for a Hewlett-Packard model 175 oscilloscope 36. The oscilloscope screen 39 was the visual output from which the reflected beam intensity was determined.

Sample preparation consisted of cutting to a usable size, generally $1'' \times 2'' \times \frac{1}{2}''$, mounting on a standard $1'' \times 2''$ glass slide and polishing the upper surface. Polishing techniques varied with the samples depending primarily on how well lithified they were.

Care is to be taken on those samples that are either coarse grained or have high clay contents. The coarser samples tend to lose grains during the initial stages of polishing, resulting in holes in the polished surface. The clay in those samples which had significant clay contents absorbed the water and cutting fluids during trimming and then shrank and warped the polished surface within about 24 hours.

These problems were overcome by cementing the sandstones with (Lakeside) cement or epoxy. The thinner epoxy penetrated the sample better but the (Lakeside) cement filled the voids better. Filling the voids between the grains of the recent sediments which were tested (below described) turned out to be more important than bounding the grains so well.

In order to level the upper surface of the sample a stainless steel mirror was placed on top of the sample after it was placed in the rotatable mount. The disk was then adjusted by means of the three leveling screws on the rotatable base. The sample was horizontal when the beam reflected on the ceilings showed no movement as the sample was rotated. This leveling is checked every three or four readings to insure accurate data.

From fifty to three hundred readings were taken for each sample. The readings were taken by rotating the spectroscope table by hand until the oscilloscope indicated a minimum intensity for the reflected beam. The orientation of the sample was then read from a spectroscope vernier and recorded. It might have been expected that the reflected beam intensity would be at a minimum with the sample in two orientations separated by 180°. This was not the case except in fewer than 10 percent of the readings. It was further assumed that the minima would be equal. This also was not the case. Because of this inequality of the minima the orientation for the lower readings was recorded. In the few cases when the intensities were so nearly equal that it was impossible to determine which was the lower, both orientations were recorded.

After the reflected light readings were recorded, a glass slide was attached to the polished surface of the sample and the remainder of the sample cut away. A standard thin section of 0.03 mm thickness was then ground. This allowed microscopic examination of the polished surface except that it was now inverted. This inversion of the sample caused a rotation of 180° about the E-W axis for the observed optic axis orientation.

The long axis examination of the samples proceded as described above. The only precaution that was found to be necessary was to cut a small notch in one corner of the slide to prevent rotation between examinations.

Optic axis determination is determined as follows:

With the microscope set for coniscopic projection, the orientation of the c axis of many of the sand grains could be determined. The width of field of the objective lens determines the area of observation and this for which grains it is possible to determine the orientation of the optic axis. If the optic axis emerges outside the field of vision, a flash figure is observed. From its movement the quadrant in which the optic axis is located can be determined.

It should be pointed out however, that the microscope measurement is more sensitive to grains whose optic axis are close to vertical while the reflected light method emphasizes those whose optic axis are nearly horizontal. If the sample is taken from an environment where deposition was on a sloping surface whose dip was not parallel to the flow direction a significant difference between the microscope and reflected light data is to be expected.

To determine the orientation of the optic axis, the microscope stage was rotated until the optic axis was in the north half of the field of view and on the N-S cross hair of the microscope. The orientation was then read from the vernier and recorded. Because the microscope used in this study has an inverting field of vision the optic axis appeared to emerge 180° from where it actually emerged. This rotation was about a vertical axis and was important when non-symmetrical properties were being measured. This inversion was not important in the long axis data.

For multiple grain optic axis determination the Metrologic Instruments photocell was connected to the occular of the (Leitz) microscope. A gypsum plate filter was put in the microscope as was a piece of transparent red plastic. The gypsum wedge caused the quartz to be blue when the optic axis was oriented NE-SW and yellow when NW-SE. The red plastic preferentially absorbed the blue portion of the spectrum from the microscope source light. Thus the light transmitted to the photocell had a minimum intensity when the optic axis was oriented NE-SW. Since many grains were being examined at once the transmitted light had a minimum intensity when the average optic axis orientation was NE-SW.

The thin sections were examined with a ten power objective and eight power occular. Fifty to one hundred readings were taken for each sample. It was expected that there would be two minimums 180° apart. This was found only rarely and again, as in the reflected light data, only the minimum intensity orientation was recorded.

Figures 13, 14:
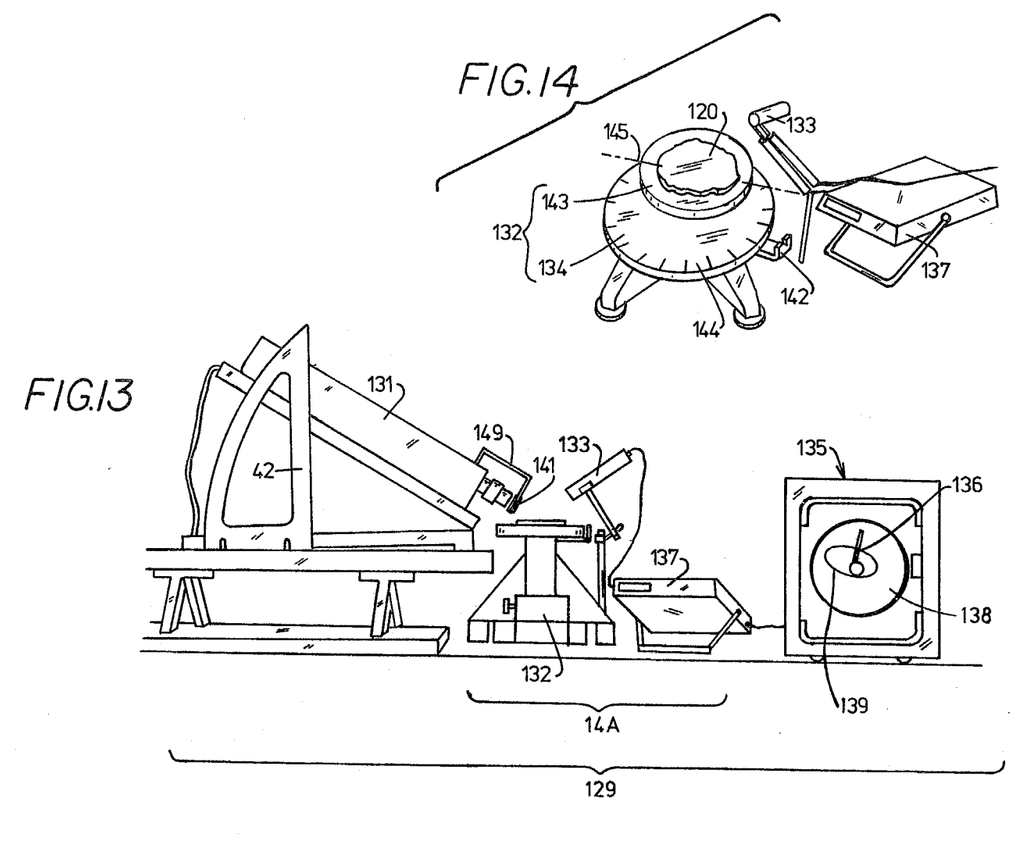
FIG. 13 is a diagramatic showing of another embodiment of equipment according to this invention.
FIG. 14 is a perspective oblique top view of the apparatus shown in portion 14A of FIG. 13.

The correct angle of incidence was set up in the lab by measuring the base and altitude of the right triangle formed by the equipment (FIGS. 1 & 13). If all the error is assumed to be in the base measurement there is an allowable error of 1.53 mm. The adjustable support 42 for the generator 131 provides for adjustment of angle of beam thereof on to the surface of 120 at angle equal to Brewster's angle in FIG. 13 apparatus.

In the ideal case the reflected beam intensity is zero, but for the work done in this process it is only a minimum.

The statistical treatment of the data included a Rayleigh test for the probability of obtaining a resultant vector of greater length from a random distribution[9], (as taught in Potter, P. E. and Pettijohn, F. J., *Paleocurrents and Basin Analysis*, p. 263–268 Academic Press Inc., 1963), then calculating the resultant vector and constructing histograms with 20°, 30°, and 40° intervals. All calculations were made by computer and the vector resultant calculations were verified by calculator.

The first part of the print out contained the Rayleigh test results for the laser and test data. The second part contained the resultant vector angle and length, the variation in the x and y components of the resultant and the standard deviation. The standard deviation was calculated as the square root of the sum of the variations in the x and y components. This type standard deviation was used because although each data entry was assigned a unit length the deviations in the calculated resultant can not be restricted to an angular variation along the arc of the resultant radius. Both the x and y components of the vector have a variation and the standard deviation of the resultant is the square root of the sum of these variations. Geometrically this standard deviation is a circle whose center has the coordinates of the resultant vector and whose radius is the standard deviation.

The print out also showed each set of data grouped into 72 5° blocks. The blocks for the test data were scanned for maximum number of data points within the desired interval. As an example the 20° block containing the maximum number of data points may be the 20th interval, from 95° to 115°. Both sets of data were then grouped into intervals so that the test data contained this maximum number. In the above example the histograms would begin at 15° and be blocked each 20° from there. The test start index number tells which 5° block the histograms are to begin on. Since the number of readings for each sample varied the histograms were constructed as percent in each interval.

Since the reflected light method depended on averaging the optic axis orientation of the individual sand grains, it was believed that histograms of data collected by the individual grain and multiple grain methods of optic axis determination would within limits of numbers of sample serve to check the reflected light data.

For the long axis data only the data in a 180° range was used. The 0°–180° line was constructed through the minimum of the long axis histogram and then the result calculated. The result was calculated by assigning a length equal to the number of data points in each interval to its midpoint value and then solving for the resultant vector. This method is not as accurate as calculating the resultant from the individual values but it is faster. These calculations were done by calculator. All other resultants are the resultants of the individual data points.

Unconsolidated samples were removed from the creek beds as cores using soft drink cans. The bottoms were cut from the cans, then they were pushed down into the sediment. Orientation of the sample relative to the stream flow direction was a simple matter of always placing the can so that the pop top opening was on the down stream side. The samples were then dried for 10–36 hours in an oven at about 300° F.

Sample Number 2 was fine grained so it was consolidated with Bear brand epoxy. The epoxy was thinned with toluene and then poured into the cans until it began to run out the bottom. These samples were at about 100° F. when the epoxy was poured on them. It had earlier been found that the higher temperatures drove off the toluene and allowed the epoxy to set in a few hours rather than days.

Orientation of all samples was maintained after removal from the cans by using a hacksaw to cut a notch in the downstream side. Slabs for examination were cut from the samples using the hacksaw. Use of a good quality 12 or 18 tooth per inch blade is recommended. The coarseness of the blade depends on the coarseness of the sediment. Blades never lasted longer than cutting one slab or removing one sample from a can and inexpensive blades did not last that long. The inexpensive blades lost their set and break up the sample because of not cutting themselves enough clearance.

Tests of samples were made by apparatus of FIG. 1 and as above described; results were obtained FIGS. 3–12 and tabulated in Table 1.

The samples for FIGS. 3–8 were cut from a concretion in the Trujillo Formation, Randall County, Texas (as source 1) the concretions were cone shaped and cemented with an iron rich clay. All samples were mounted with the base of the cone down. This is upside down to their field orientation and thus plotting the minima produced a downstream histogram.

Figures 3, 5:
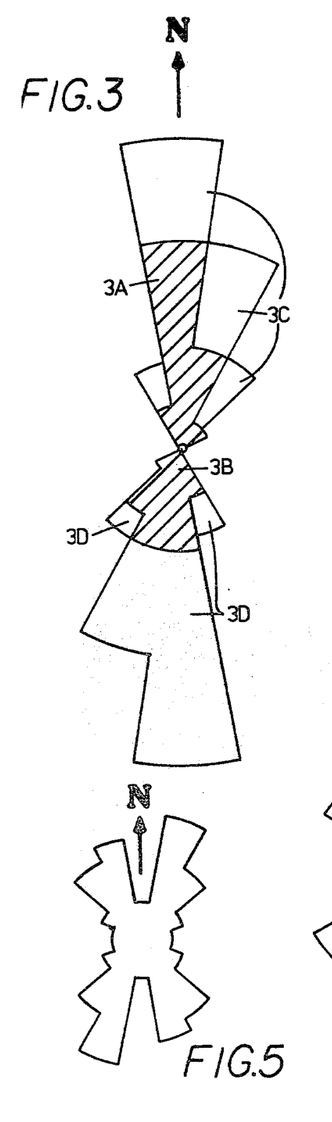
FIG. 3 is a diagramatic but scale showing of the laser data obtained on one portion of sample number 1 with histogram interval of 20°.
FIG. 5 is a diagramatic showing of long axis data, with histogram interval of 20°, on the same portion of sample number 1 referred to in FIGS. 3 and 4.
Figures 4, 6:
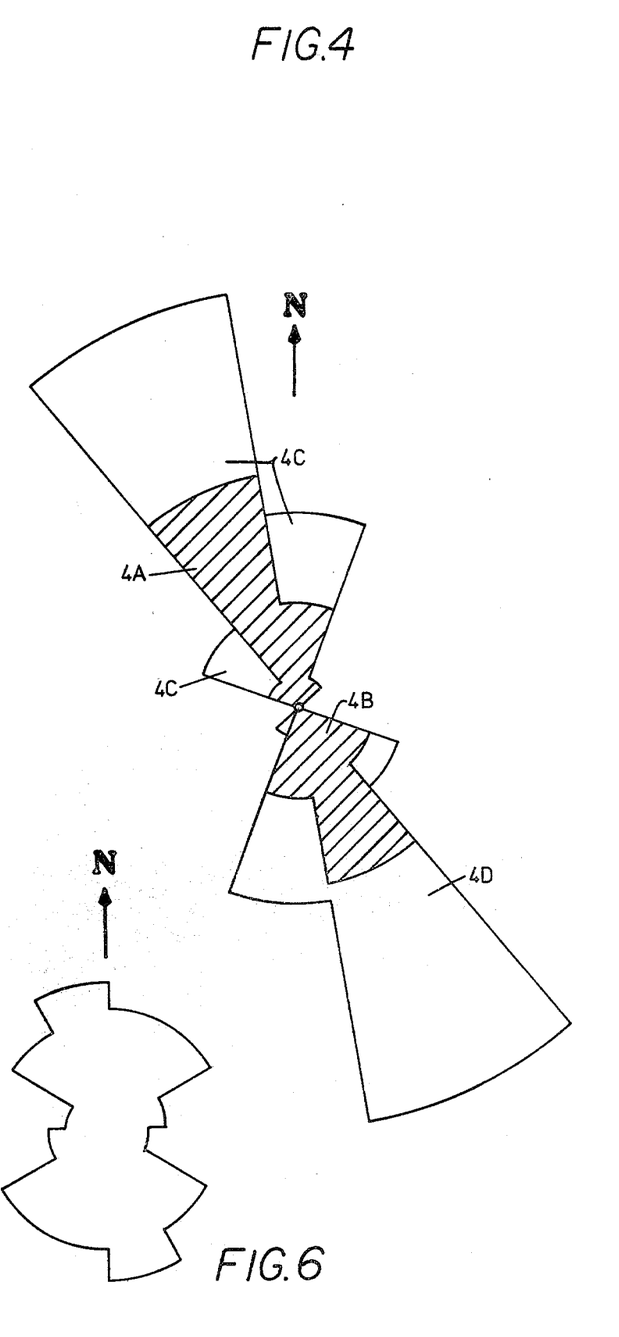
FIG. 4 is a diagramatic scale showing of the laser data obtained on the same portion of sample number 1 with a histogram interval of 30°.
FIG. 6 is a diagramatic showing of the same long axis data used in FIG. 5 but with a histogram interval of 30°.
Figure 7:
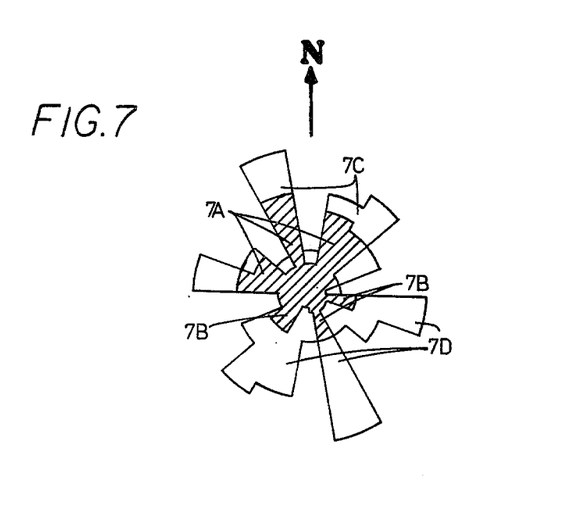
FIG. 7 is a diagramatic but scale showing of a histogram provided from laser data, with a histogram interval of 20°, on another portion of sample number 1.
Figure 8:
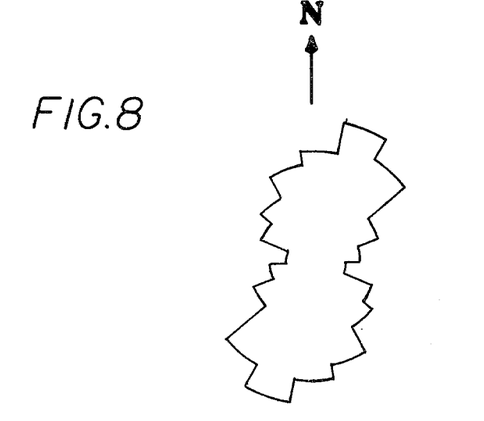
FIG. 8 shows long axis data on the same portion of sample number 1 as shown in FIG. 7 but with histogram interval of 20°.
Figure 9:
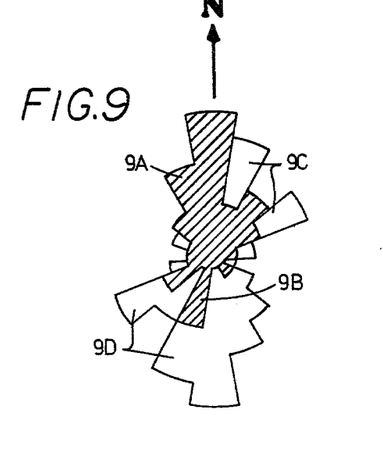
FIG. 9 is a diagramatic but scale showing of the laser data obtained on one portion of sample number 2 with a histogram interval of 20°.
Figure 10:
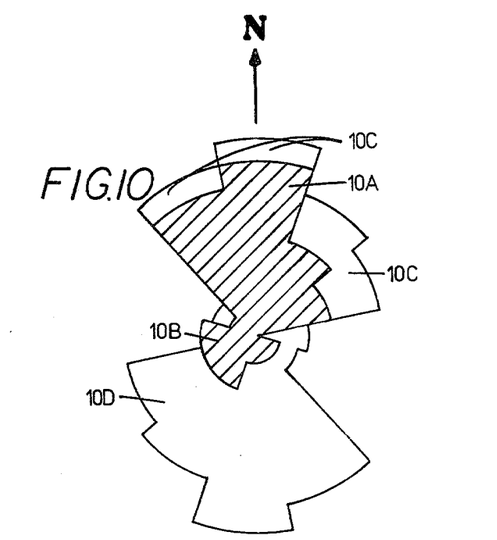
FIG. 10 is a diagramatic scale showing of the laser data obtained on the same portion of sample number 2 as in FIG. 9 but with a histogram interval of 30°.
Figure 11:
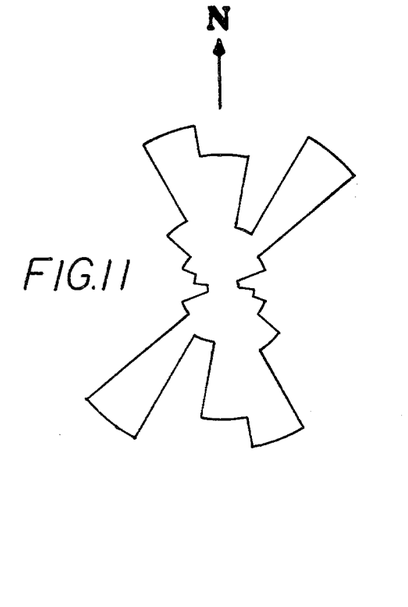
FIG. 11 is a diagramatic showing of long axis data, with histogram interval of 20°, on same portion of sample number 2 referred to in FIGS. 9 and 10.
Figure 12:
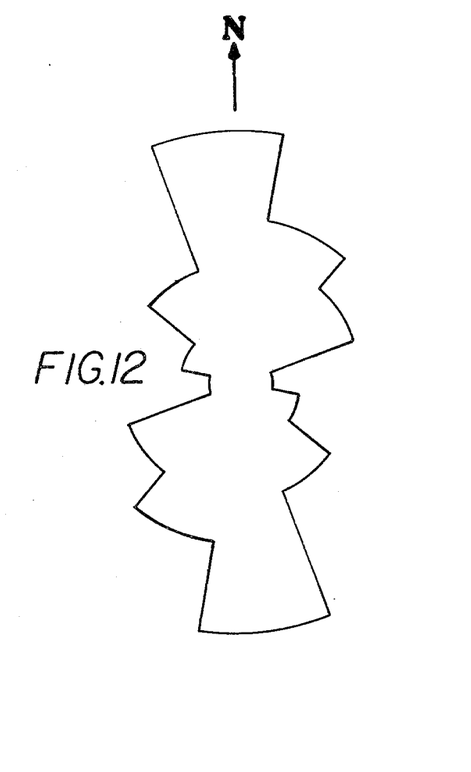
FIG. 12 is a diagramatic showing of the same long axis data as used in FIG. 11 but with a histogram interval of 30°.

In this group the reflected light histograms of FIGS. 3, 4, and 7 are given with long axis histograms as the only test data. The approximate paleocurrent direction is known as 174° with standard deviation of 27° from the sedimentary structure work of Cramer (Cramer, S. J., Paleocurrent Analysis of the upper Triassic Sandstones of the Texas High Plains, unpublished Master Thesis, West Texas State University, 1973) and as 173° with standard deviation of 28° from work of Cramer and Asquith (Asquith, G. and Cramer, S. J., Transverse Braid Bars in the Trujillo, J. of Geol., v. 83, pg, 657–661, 1975).

Source 2 is an initially unconsolidated sand core from a tributary to the Prairie Dog Fork of the Red River, Randall County Texas and had a stream direction of 180° (due north).

In Table 1 the laser data is presented in two forms. At Col. 6 each of columns 2, 5 and 7 is the vector resultant of all the readings taken for that sample. The following columns show the result of considering the readings separated by 180° as equivalent and adding the number of readings in opposite intervals to get a symmetrical graph for 20° and 30° histogram intervals.

The results of the values obtained by the herein above described method are seen to be very close to the value obtained by more tedious methods, and closer than results obtained by long axis measurements (which does not give direction) and more significant than the histogram presentations.

It is absolutely imperative that top and bottom orientation be maintained during the removal and preparation of the samples. Inversion of the sample will result in reversing the stream flow direction.

The apparatus of FIG. 13 comprises, in operative combination, a laser beam generator 131 with an output of $3\frac{1}{2}$ milliwatts, photoresistor 133 of a one inch diameter cross section area transverse to the detected beam length, a rotatable support table 132 for the specimen 120, a circular recorder 135. The chart drive mechanism of recorder 135 is "slave" to or controlled by the movement of the table 132 and the recording mechanism 136 is controlled by the photoresistor resistance by conventional resistance sensitive controls and motor drive.

The drive mechanism for the specimen as 120 may be manual as by arm 142 which moves the rotatable support table 143 and also indicates on scale 144 the position of the axis 145 of the specimen 120. An ohmmeter 137 is connected to the photoresistor 133 and provides digital reading of its resistance. The pen-bearing arm 136 of the recorder 135 moves radially inversely to the light intensity of the beam striking photoresistor 133. The arm 136 bears a pen or other indicating instrument which records on the chart 138 and provides a record at path 139 on the chart. In a preferred embodiment, a lens or an elliptical orifice 141 is held in the light path between the laser output and the sample. The laser provides a large diameter beam (one-inch by three quarter inch cross section) while maintaining sufficient intensity to reliably trigger photoresistor in the ambient light situation in which the apparatus 129 is used. Total darkness is not necessary for operation of the apparatus. Arm 149 supports orifice 141.

Figures 15, 17, 18:
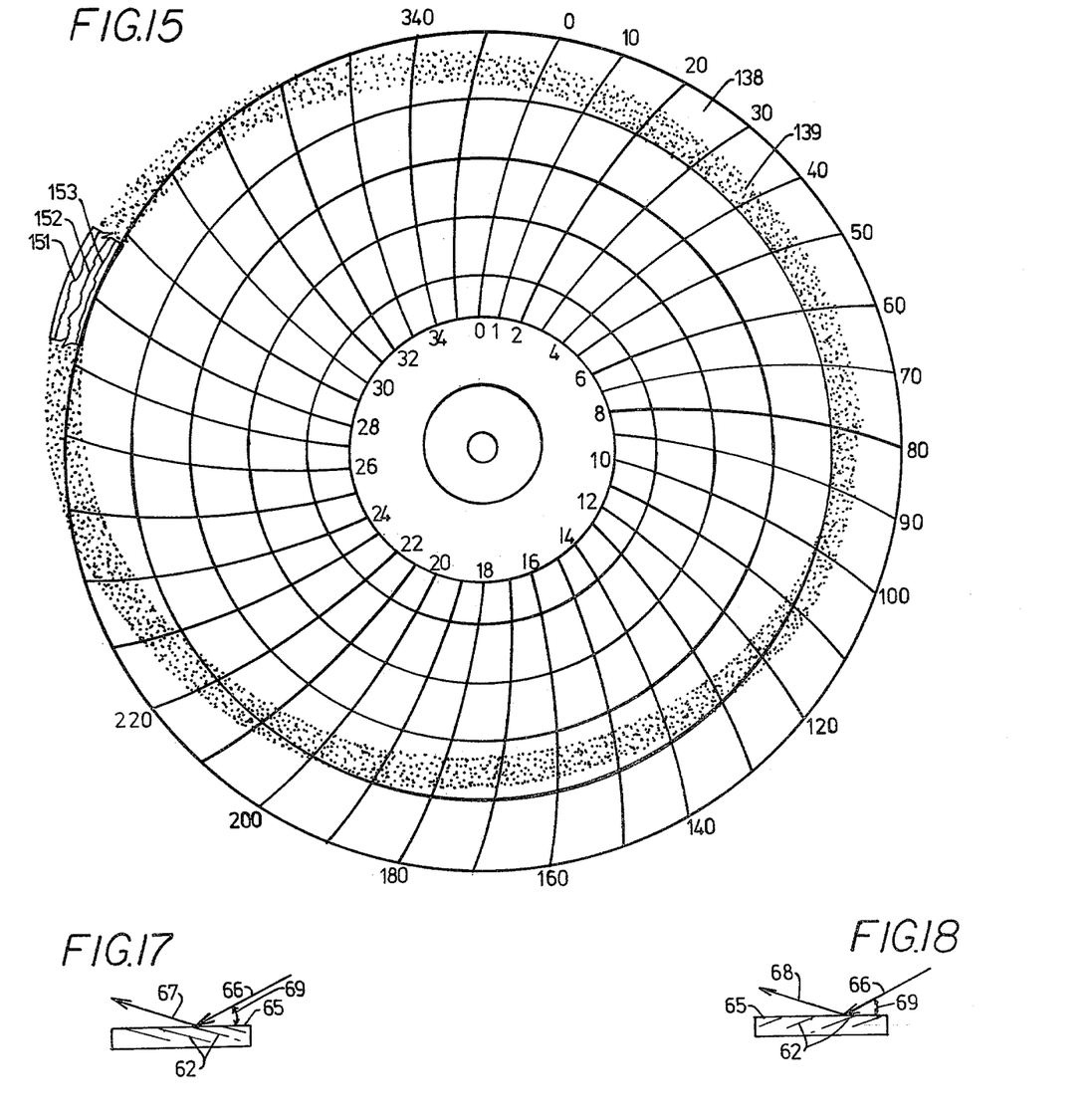
FIG. 15 is a copy of a circular chart of laser data obtained according to the process of this invention using the apparatus shown in FIGS. 13 and 14.
FIGS. 17 and 18 are diagramatic representations of the relations of incident and reflected light beams and optic axis in a polished specimen from samples from a bed as in FIG. 16.

FIG. 15 shows the path 139, [of readings which rapidly and conveniently provides a very large number of readings]; in this case a sidementary stream bed was tested and, as shown in FIG. 15, the sample tested by apparatus 129 provides a minimum light intensity at 290°. As the sample was inverted about a North-South axis, the direction of stream flow was North 70° East for this case, in demonstration of use of the apparatus 129 for the method of paleocurrent direction determination above described. In FIG. 15 the band shown as 139 is composed of many (11) closely spaced paths, as (151, 152, 153) or tracings. The paths are shown as one group in a stippled band to show the overall shape of paths as (151–153) and the close agreement of results obtained by repeated tests of a sample by apparatus 129. The large diameter beam allows rapid analysis of large grain sediments (greater than 2.5 mm average diameter) because there is an inverse relation between the number of grains whose optic axis orientation are averaged and the variation in the data. The larger beam significantly reduces the number of readings necessary. It also is especially useful for large grain sediments deposited under turbid flow conditions or on the face of sand bars where the grain orientation is not uniform, as such orientation is a function not only of the current direction but also of depositional surface orientation.

The large photocell with a large diameter beam also has the secondary result that its output is less sensitive to wandering of the reflected beam. Although such wandering is to some degree inevitable because, even if the table were perfectly horizontal the polished surface of samples have some variations: these slight variations do not cause any detectable false readings.

The combination of movable table and strip chart recorder moving at the same linear speed and/or with the same linear displacement between readings provide easier and faster readings and a permanent record of the variations in the reflected light intensity as a function of sample orientation as shown in FIG. 15. Easier operation is of value when large numbers (200-300) of readings are to be taken on each sample and large numbers of samples are to be run. The permanent record is essential not only for accurate determination of sample orientation at minimum readings but also the wave form of the reflected light intensity variation may be checked thereby for consistency in each sample. Large variations in wave form are usual indications of equipment malfunction. Visual estimation of this variation is one of the best indicators that the sample was not level.

The beam leaving the laser has a circular cross section but as it intersects the sample it has an elliptical cross section. Because of this as the sample is rotated the beam is reflected from two sets of grains. The set of grains defined by the inner radius of the ellipse is reflecting light continually as the sample is rotated, but each radial segment of the set of grains between the inner and outer radius reflects only twice per rotation. The total intensity of the reflected light is thus not a simple function of the average optic axis orientation but is a combination of this and which grains are reflecting. This situation is corrected by placing an elliptical orifice or appropriately ground lens in the light path. This use of apparatus provides a beam of elliptical cross-section shape transverse to the length of the beam, which beam thus intersects the sample surface at a circular shaped area.

Figure 16:
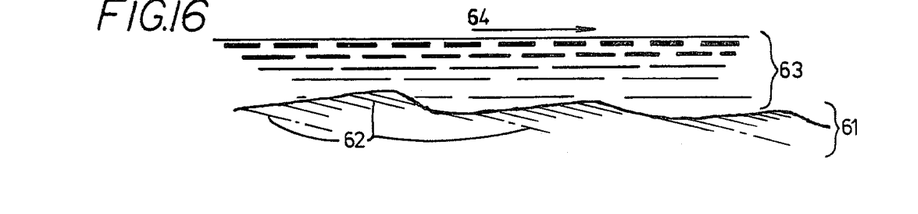
FIG. 16 is a diagramatic representation of stream flow past a sedimentary rock bed and orientation of the grains in that stream bed.

Generally, as diagramatically shown in FIGS. 16, 17, and 18, the direction of the optic axis and crystal elongation, as 62, in quartz grains in a bed, 61, past which a stream, 63, flows in a given direction, 64, is at an acute angle downward and in the forward direction (64) of down stream flow of the stream and at an acute angle to the plane parallel to the direction of stream flow and in the forward direction (64) of down stream flow of the stream, 63.

The intensity of the beam reflected as 67 from an incident beam 66 at a given angle as 69 to polished surface 65 is at a minimum when the plane of beams 66 and 67 coincide with the plane of the grain optic axis as 62, and the intensity, (at the same angle 69 of incident beam 65) of reflected beam as 68 is different when the incident beam 66 meets a different combination of horizontal and vertical plane components of the optical axes of the grains tilted generally in the opposite direction as diagramatically shown in FIG. 18. The action on the reflected beam as shown in FIG. 17 produces one minimum in reflected light reading at photocell 33 photoresistor 133 and the action at FIG. 18 produces the other minimum with the minimum in the down stream direction being a more pronounced minimum than in the other direction. Thereby the direction of stream flow as well as the line in the plane in which it lies is determined by the method herein above described and apparatus as provided therefor.

TABLE I

INSERT A:

| Row No. | | Column No. 1 | 2 | 3 | 4 | 5 | 6 | 7 | 8 | 9 |
|---|---|---|---|---|---|---|---|---|---|---|
| 1 | Sample # | 1 | 1 | 1 | 2 | 2 | 1 | 1 | 1 | |
| 2 | Source | 1 | 1 | 1 | 1 | 1 | 2 | 2 | 2 | |
| 3 | Number of Readings | 50 | * | * | 50 | * | 30 | * | * | |
| 4 | Histograms Interval | | 20° | 30° | | 20° | | 20 | 20 | |
| 5 | Resultant Magnitude [L] % | 10 | 84 | 93 | 30 | 69 | 42 | 73 | 75 | |
| 6 | Resultant Angle (deg.) | 167 | 155 | 161 | 173 | 184 | 179 | 190 | 196 | |
| 7 | Drawings Figure Number | | 3 | 4 | | 7 | | 9 | 10 | |

\* = Calculated From Symmetrical Histograms

I claim:

1. Method of determining the average optic axis orientation and direction of a polished multiple grain sedimentary sample comprising the steps of:
    (a) measuring the variations in the intensity of a beam of light from a laser while said sample is at different angular positions relative to said beam and said beam is being reflected from a surface of said polished sample and while said beam of light intersects said surface at Brewster's angle, the reflected ray having a minimum intensity when the average optic axis of the sample lies in the plane of incidence of said beam, and
    (b) determining the direction of minimum intensity of the reflected ray relative to the orientation of said sample from which said sample is taken and thereby determining the optic axis orientation and direction of said sample.

2. Method as in claim 1 whereas the sample comprises quartz grains.

3. Method as in claim 1 comprising also the steps of forming an asymmetric histogram representative of the position and amount of said measured variations in intensity of said ray, said histogram having two portions of unequal length, one portion extending at less than 180° to the other, and both portions extending from a common center, and measuring the direction of said optic axis from the histogram portion of lesser length to the center of the histogram to determine said optic axis orientation and direction.

4. Method of determining paleocurrent direction of a sedimentary multiple grain structure, said structure represented by a multiple grain sample with a polished surface, comprising the steps of:

(a) measuring the variations in the intensity of a beam of light from a laser while said sample is at different angular positions relative to said beam and said beam is being reflected from a surface of said polished sample and while said beam of light intersects said surface at Brewster's angle, the reflected ray having a minimum intensity when the average optic axis of the sample lies in the plane of incidence of said beam from said laser, (b) determining the direction of minimum intensity of said ray relative to the orientation of said sample from which said sample is taken and thereby determining the paleocurrent direction of said structure.

5. Process as in claim 4 whereas the wave length of said laser beam is 6328 A.

6. Process as in claim 5 whereas in said intensity of said ray is measured by a moving recorder and the sample is rotated at a speed proportionate to the speed of movement of the recorder while the surface is maintained at a constant solid angle relative to said beam.

7. Method as in claim 6 comprising also the steps of forming an asymmetric histogram representative of the position and amount of said measured variations in intensity of said ray, said histogram having two portions of unequal length, one portion extending at less than 180° to the other and both portions extending from common center, and measuring the direction of said optic axis from the histogram portion of lesser length to the center of the histogram to determine said optic axis orientation and direction.

8. Method as in claim 7 wherein said beam is 3/4 inch wide in one direction measured transverse to the length of the beam.

9. Apparatus for anisotropic mineral grain orientation comprising, in operative combination, a laser beam generator, photo sensitive means, a rotatable specimen support table, a flat surface specimen on said support, a quantitative light intensity recorder, a drive mechanism for said recorder with movement means therefor controlled by the movement of said table and recording means of said recorder controlled by the photo-sensitive means, an adjustable support for said laser beam generator, said specimen comprised of a plurality of anisotropic grains each elongated parallel to its optical axis, said laser beam directed at the surface of said specimen at Brewster's angle relative to said surface, said laser beam having a greater diameter than the individual length of said grains.

10. Apparatus in claim 9 comprising an adjustable support for said laser beam generator.

11. Apparatus as in claim 10 comprising an elliptical orifice in the light path between the laser output and the specimen.

12. Apparatus as in claim 11 wherein the said support and said recorder are operatively connected to drive means therefor whereby to be driven at linear porportionate speeds relative to each other.

* * * * *